United States Patent

Abou-Gharbia et al.

Patent Number: 4,719,211
Date of Patent: Jan. 12, 1988

[54] 2,3,4,9-TETRAHYDRO-2-HETEROARYLALKYL-1H-PYRIDO(3,4-B)INDOLES HAVING ANTIHYPERTENSIVE PROPERTIES

[75] Inventors: Magid A. Abou-Gharbia, Wilmington, Del.; Meier E. Freed, Bryn Mawr, Pa.

[73] Assignee: American Home Products Corporation, New York, N.Y.

[21] Appl. No.: 837,612

[22] Filed: Mar. 7, 1986

Related U.S. Application Data

[63] Continuation-in-part of Ser. No. 605,944, May 1, 1984, abandoned.

[51] Int. Cl.$^4$ .................. A61K 31/495; C07D 471/06
[52] U.S. Cl. ..................................... 514/253; 514/227; 514/254; 514/292; 544/120; 544/126; 544/295; 544/361; 544/363; 544/364; 544/405; 544/406; 546/84; 546/85; 546/87
[58] Field of Search ............... 544/120, 126, 295, 405, 544/406; 546/84, 85, 87; 514/253, 292

[56] References Cited

U.S. PATENT DOCUMENTS

| | | | |
|---|---|---|---|
| 4,272,539 | 6/1981 | Koletar et al. | 514/292 |
| 4,361,566 | 11/1982 | Van Dyke, Jr. et al. | 514/292 |
| 4,431,649 | 2/1984 | Welch et al. | 546/87 |
| 4,663,456 | 5/1987 | Abou-Gharbia | 544/361 |

OTHER PUBLICATIONS

Derwent Abstract No. 14,306F of Japanese Kokai No. 22853, published Oct. 14, 1964, to Fujisawa Pharm. Co., Ltd.

Primary Examiner—Donald G. Daus
Assistant Examiner—Cecilia Shen
Attorney, Agent, or Firm—Arthur G. Seifert

[57] ABSTRACT

This invention concerns tetrahydropyridoindoles of the formula:

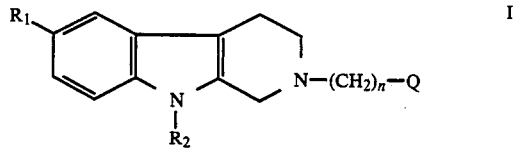

wherein Q represents

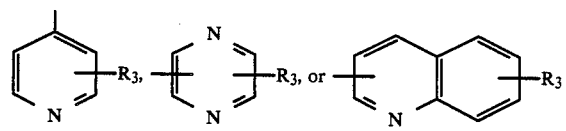

in which $R_3$ is hydrogen, $C_{1-4}$ alkyl, $C_{1-4}$ alkoxy, or —COO($C_{1-2}$) alkyl, and n is an integer from 1 to 7; $R_1$ is hydrogen, halogen, hydroxy, or $C_{1-3}$ alkyl; and $R_2$ is hydrogen, $C_{1-4}$ alkyl or —(CH$_2$)$_m$—A where A is —N(CH$_3$)$_2$,—N(C$_2$H$_5$)$_2$,

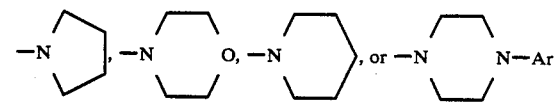

in which Ar is 2-pyrimidinyl, 2-pyrazinyl, phenyl, or phenyl substituted by a methyl, ethyl, methoxy, ethoxy, or trifluoromethyl group; and m is an integer from 1-4, or physiologically acceptable salts thereof, providing however that when n is 1, Q may not be quinolinyl. These compounds exhibit antihypertensive properties. Four of the disclosed compounds also exhibit antipsychotic properties.

Also disclosed are compounds of Formula XX in which Q of Formula I is replaced by $Q_1$, wherein $Q_1$ is 2- or 3-pyridinyl, and $R_2$ of Formula I is restricted to hydrogen. The compounds of Formula XX exhibit antipsychotic properties.

21 Claims, No Drawings

2,3,4,9-TETRAHYDRO-2-HETEROARYLALKYL-1H-PYRIDO(3,4-B)INDOLES HAVING ANTIHYPERTENSIVE PROPERTIES

SUMMARY OF THE INVENTION

This application is a continuation-in-part of application Ser. No. 605,944, filed May 1, 1984, now abandoned. This invention concerns tetrahydropyridoindoles of the formula:

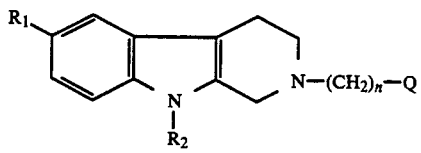

wherein Q represents

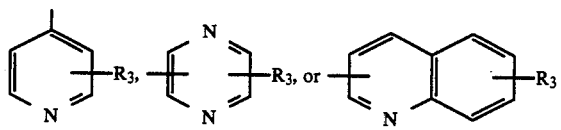

in which $R_3$ is hydrogen, $C_{1-4}$ alkyl, $C_{1-4}$ alkoxy, or —COO($C_{1-2}$) alkyl, and n is an integer from 1 to 7; $R_1$ is hydrogen, halogen, hydroxy, or $C_{1-3}$ alkyl; and $R_2$ is hydrogen, $C_{1-4}$ alkyl or —(CH$_2$)$_m$—A where A is —N(CH$_3$)$_2$, —N(C$_2$H$_5$)$_2$,

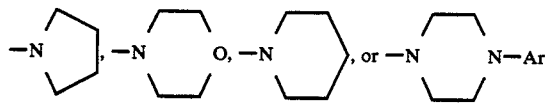

in which Ar is 2-pyrimidinyl, 2-pyrazinyl, phenyl, or phenyl substituted by a methyl, ethyl, methoxy, ethoxy, or trifluoromethyl group; and m is an integer from 1–4, or physiologically acceptable salts thereof, providing however that when n is 1, Q may not by quinolinyl.

The compounds of Formula I of the invention exhibit antihypertensive properties in standard pharmacological tests. The compounds of this invention are useful for treating hypertension in a mammal by administering to a mammal in need thereof an effective antihypertension amount of a compound of Formula I or physiologically acceptable salt thereof.

The compounds of Examples 3, 4, 5, and 8 also exhibit pharmacological properties as antipsychotic agents.

A further aspect of the invention provides compounds of Formula XX having the structural formula of Formula I but with Q replaced by $Q_1$, wherein $Q_1$ is 2- or 3-pyridinyl, and with $R_2$ restricted to hydrogen. The compounds of said Formula XX exhibit pharmacological properties as antipsychotic agents.

The compounds of Examples 9, 10, 11, 12, 13 and 14 exhibit pharmacological properties as antipsychotic agents.

BACKGROUND OF THE INVENTION

The present invention (per Formula I) relates to novel tetrahydro-1H-pyrido[3,4-b]indoles having a 4-pyridinylalkyl, 2-pyrazinylalkyl, or 2-, 3-, or 4-quinolinylalkyl substituent attached to the pyrido nitrogen. The compounds may be substituted on the benzene ring of the nucleus and at the indole nitrogen. The 4-pyridinyl, 2-pyrazinyl, and 2-, 3-, or 4-quinolinyl rings may also be optionally substituted ($R_3$). The compounds of the invention are useful as antihypertensive agents. The invention also includes pharmaceutical compositions having said compounds as the active ingredient and a method of treating hypertension by administering an antihypertensive effective amount of a compound of the invention to a mammal in need of antihypertensive treatment.

The present invention (per Formula XX) further relates to novel tetrahydro-1H-pyrido[3,4-b]-indoles having a 2- or 3-pyridinylalkyl substituent attached to the pyrido nitrogen. These compounds may be optionally substituted on the benzene ring of the nucleus but have only hydrogen on the indole nitrogen. The compounds of the aspect of the invention are useful as antipsyhchotic agents. This aspect of the invention also includes pharmaceutical compositions having said compounds as the active ingredient and a method of treating psychosis by parenterally administering an anti-psychotically effective amount of a compound of this aspect of the invention to human or animal in need of psychotropic therapy.

The 2,3,4,9-tetrahydro-1H-pyrido[3,4-b]indole nucleus of the compounds of the invention is also referred to as a tetrahydro-β-carboline nucleus. The closest prior art disclosure of such tetrahydro-β-carboline derivatives to Applicants' compounds of Formula I of the invention are described in the Japanese Kokai No. 22853, published on Oct. 14, 1964, to Fujisawa Pharmaceutical Co. Ltd., which is found in Derwent Abstracts No. 14306F. The β-carbolines of this Fujisawa Japanese patent disclosure have an aminopropyl or N-heteropropyl substituent on the pyrido nitrogen of the β-carboline nucleus and are described as being sedatives and anti-hypertensives. The Fujisawa compounds, therefore, differ from Applicants' compounds in having the alkylene bridge attached to the nitrogen of an amino or a non-aromatic heterocyclic group. Applicants' compounds have a monocyclic or bicyclic aromatic nitrogen heterocyclic group attached at the distal end of the alkylene bridge, with said attachement being to a carbon atom instead of the nitrogen heteroatom.

DETAILED DESCRIPTION OF THE INVENTION

Preferred compounds of the invention of Formula I are those in which n is 2, 4, or 7; $R_1$ is hydrogen or fluorine; $R_2$ is hydrogen; or $R_3$ is hydrogen. Also preferred are compounds in which Q is pyrazinyl or 2- or 4-quinolinyl. Other preferred $R_2$ groups are those in which A is dimethylamino, diethylamino, morpholinyl, or pyrazinyl wherein Ar is 2-pyrimidinyl or 2-pyrazinyl. In such groups where $R_2$ is —(CH$_2$)$_m$—A, m is 3 is preferred. With respect to antihypertensive properties, preferred compounds of the invention are those of Examples 2, 4, 5, 6, and 7.

Preferred compounds of the invention of Formula XX are those in which n is 2, 3 or 4 and $R_1$ is hydrogen or halogen. The preferred halogen for $R_1$ of the compounds of Formula XX is flourine. Preferred compounds of this aspect of the invention are those of Examples 9, 11 and 13.

As used herein, "alkyl", "lower alkyl", "alkoxy", "lower alkoxy", or "alkylene" refer to such hydrocarbon groups having 1-7 carbon atoms, unless otherwise specified. Generally, such groups having 1-4 carbon atoms are preferred. "Halogen" refers to fluorine, chlorine, bromine, or iodine, of which fluorine and chlorine are preferred with regard to antihypertensive characteristics of the compounds of the invention.

As shown in Scheme 1 below, the compounds of Formula I of the invention wherein $R_2$ is hydrogen and the compounds of Formula XX of the invention are prepared by the reaction of the equimolar amounts of the desired 2,3,4,9-tetrahydro-pyrido[3,4-b]indole II and either a haloalkylpyridine, haloalkylpyrazine or haloalkylquinoline III (route 1a) or a vinylpyridine, vinylpyrazine, or vinylquinoline IV (route 1b), in which $R_1$, n, and Q are as previously defined.

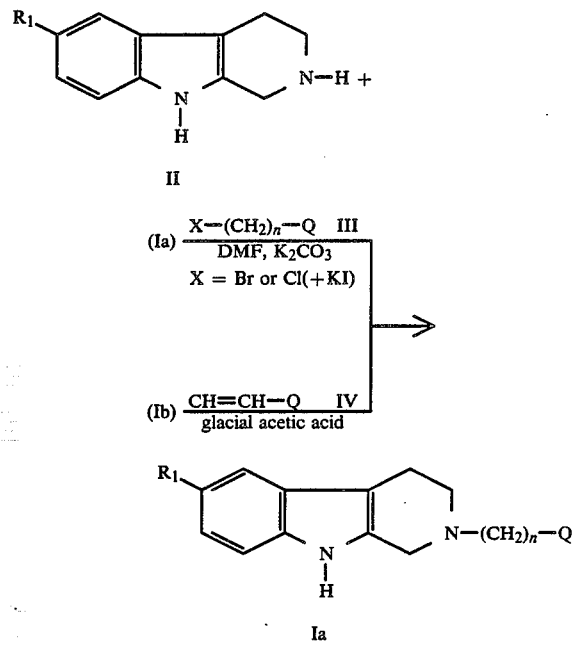

The nucleophilic substitution reaction (1a) is run in an aprotic solvent, such as dimethylformamide (DMF), dimethyl sulfoxide (DMSO), acetone, or alcoholic acetonitrile, in the presence of a mild base (acid scavenger), such as sodium, potassium or cesium carbonate. The halide X is preferably bromine. When chlorine is used instead, a small amount of potassium iodide may be added as a catalyst. The reaction is conveniently carried out at room temperatures (20°-30° C.) for 4-24 hours, 12-24 hours being preferred. A shorter alkylene chain in the halide reactant and elevated temperatures, allow reaction time to be decreased.

The vinyl addition reaction (1b) may be used where compounds of the invention having n=2 are desired. The reactions are conveniently run in an alcoholic solvent, preferably methanol or ethanol, in the presence of a catalytic amount of glacial acetic acid. These reactions are preferably run at a solvent reflux temperatures for 4-24 hours, 12-24 being especially preferred.

Where $R_2$ other than hydrogen is desired, the desired compound of Formula Ia is first reacted with a strong base, such as sodium hydride in DMF or DMSO or lithium amide in liquid ammonia or tetrahydrofuran. This reaction is followed closely by the addition of an alkylhalide or an alkylenehalide of the formula $X(CH_2)_m$—A, where A and m are as previously defined. The reaction with the strong base is run at room temperatures (25° C.) for about 30 minutes or until the evolution of hydrogen gas ceases. The alkylhalide ($R_2=C_{1-4}$ alkyl) or alkylenehalide ($R_2=-(CH_2)_m$—A) is thus added and this reaction is run for 2-24 hours at temperatures of 25°-60° C. Slightly elevated temperatures of 25°-40° C. are preferred with a reaction time of 12-24 hours. The reaction time required for complete reaction depends upon the length of the alkylene chain and the reaction temperature, a longer alkylene chain and a lower temperature requiring longer reaction times. The halide used in the above-described alkylhalide or alkylenehalide may be bromide, chlorine, or iodine. Bromine is preferred, and when chlorine or iodine is used, a small amount of potassium iodide may be added as a catalyst. Such as alkylation reactions are described in U.S. Pat. No. 3,142,678, issued July 28, 1964, to Rice and Freed.

The starting 2,3,4,9-tetrahydropyride[3,4-b]indoles (II in Scheme 1 above) are prepared from substituted tryptamines (V in Scheme 2 below) or indole-2,3-dicarboxylic acid anhydrides (VII in Scheme 3 below), following known literature procedures (Journal of Pharmaceutical Science, 1969, 58, 998; Journal of Medicinal Chemistry, 1983,26,499; and Z. Naturforsch, 1976,31B,589).

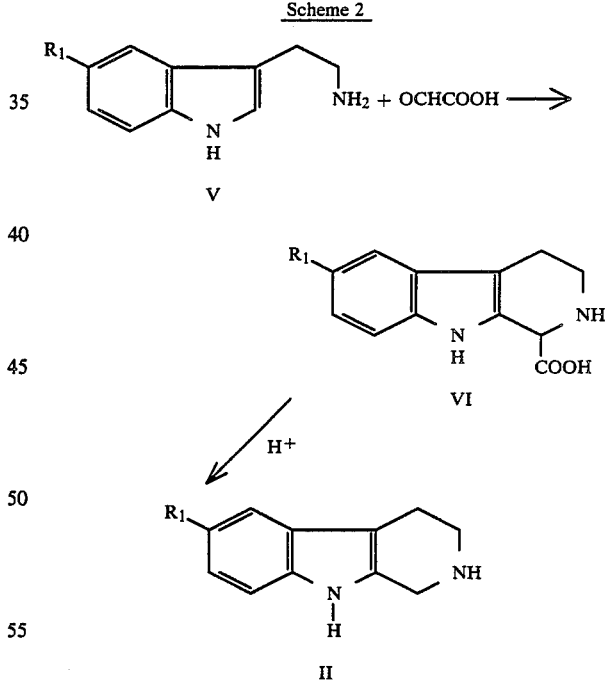

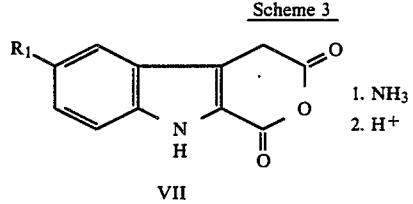

-continued
Scheme 3

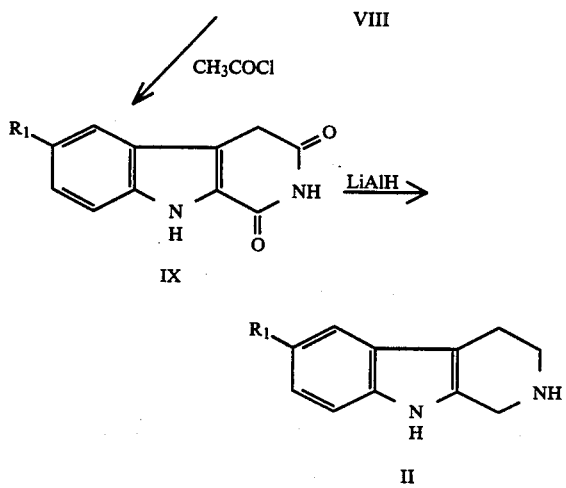

The compounds of Formula I or of Formula XX may exist either in the form of the free base or an acid addition salt thereof. Methods of converting the free base to a salt or vice versa are well known in the art. Particular salts may be utilized by the medicinal chemist for purposes of isolating and/or characterizing a compound of Formula I (or an intermediate compound).

For pharmacological and therapeutic use the compounds of Formula I or Formula XX may be used or administered in the free base form or as a physiologically acceptable acid addition salt. The preparation and use of such salts is well known in the art. Examples of appropriate salts are those formed from the following inorganic and organic acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, madelic, cinamic, palmitic, itaconic, and benzenesulfonic.

The invention includes all such acid addition salts of the compounds of Formula I or Formula XX. The physiologically acceptable acid addition salts are preferred.

The antihypertensive effect of a compound of Formula I is elicited and demonstrated by administering the compound to a hypertensive rat and measuring the change in systolic blood pressures from just prior to drug administration to 1.5, 4 and 24 hours thereafter.

The systolic blood pressure of male conscious, spontaneously hypertensive rat (SHR) (Taconic Farms) is measured by indirect tail plethysmography using a system designed and built by Narco Bio-Systems-(Model MK-IV). Groups consisting of 4 rats receive a single oral dose of the test compound. Rats are warmed in a heated chamber at 38° C. for 10 minutes prior to measurement of systolic pressure to increase the accuracy of measurements.

The systolic pressure and heart rate data are collected in an Hewlett Packard 88 computer. Data are grouped and summarized, with the mean change in pressure and heart rate at each time period calculated.

The results of such measurements for the compounds of examples are summarized in Table I below. Unless otherwise noted, the compound was tested in the form in which it was obtained in the example.

TABLE 1

| Example No. | Dose (mg/kg.) | Change in Blood Pressure (mm of Hg.) |
|---|---|---|
| 1 | 50 | −27 (1.5 hrs.); −35 (4 hrs.) |
| 2 | 50 | −79 (1.5 hrs.); −57 (4 hrs.) |
|  | 10 | −73 (1.5 hrs.); −30 (4 hrs.) |
|  | 25 | −18 (1.5 hrs.); −58 (4 hrs.) |
| 3 | 50 | −44 (1.5 hrs.); −58 (4 hrs.) |
| 4 | 50 | −105 (1.5 hrs.); −115 (4 hrs.) |
|  | 10 | −43 (1.5 hrs.); −39 (4 hrs.) |
| 5 | 50 | −98 (1.5 hrs.); −84 (4 hrs.) |
|  | 10 | −25 (1.5 hrs.) |
| 6 | 50 | −94 (1.5 hrs.) |
| 7 | 50 | −110 (1.5 hrs.); −104 (4 hrs.) |
|  | 5 | −14 (1.5 hrs.) |
| 8 |  | not tested |

The compound 2,3,4,9-tetrahydro-2-(2-quinolinylmethyl)-1H-pyrido[3,4-b]-indole, dihydrochloride (i.e. - $R_1$, $R_2$ and $R_3$ are hydrogen, n is 1, and Q is 2-quinolinyl) did not lower blood pressure significantly (−10 mm Hg at 50 mg/kg). Accordingly, compounds in which n is 1 and Q is quinolinyl are excluded from the claimed subject matter.

The antipsychotic properties of the compounds of Examples 3, 4, and 8–14 were determined by their ability to inhibit limbic D-2 dopamine receptor binding.

The assay method employed is a modification of the procedures in: J. Z. Fields, T. D. Reisine, and H. I. Yamamura: Biochemical demonstration of depaminergic receptors in rat and human brain using $^3$H-spiroperidol. Brain Res. 136:578–584, 1977; H. I. Yamamura, S. J. Enna, and M. J. Kuhar, eds., Neurotransmitter Receptor Binding, Raven Press, NY 1978.

In this procedure the test object is a rate brain homogenate which is prepared in the following manner.

Several rats are decapitated and the brains are rapidly removed. Limbic brain tissue (nucleus accumbens, septal area, olfactory tubercle) is dissected and homogenized on ice in 9 volumes of buffer (50 mM Tris-HCl, 120 mM NaCl, 5 mM KCl, 1 mM Cacl$_2$, 1 mM MgCl$_2$, 0.1% L-ascorbic acid, 10 μM pargyline HCl, pH 7.1) using a Polytron homogenizer at setting 5 for 3 15-sec bursts. The homogenate is then diluted 4-fold with buffer and centrifuged at 30,000×g for 20 min, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

The homogenate is then used in the assay in the following manner.

Thirty μl of the homogenate (0.2–0.3 mg protein/sample) are incubated with 0.3 nM $^3$H-spiroperidol (New England Nuclear) and various concentrations of test drug in a final volume of 1 ml of the above buffer for 10 min in a 37° C. water bath. At the end of the incubation, 3 ml of cold 50 mM Tris-HCl, pH 7.7, are added to each tube, and the contents are rapidly vacuum-filtered through Whatman Gf/B glass-fiber filters. The filters are then rapidly washed 3 times with 3 ml of the same buffer, placed in scintillation vials, and shaken for 15 min with 10 ml of Hydrofluor (national Diagnostics) scintillation cocktail. The vials are then counted in a Packard 460CD scintillation counter.

Specific binding is defined as total binding less binding in the presence of 1 μM (+)butaclamol. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-Spiroperidol}]}{K_D}}$$

where $K_D = 0.3$ nM for spiroperidol binding

The components are tested at concentrations up to $10^{-5}$ micromolar. Compounds having $K_i$ values of less than 100 are considered to have marked activity; $K_i$ of 100–1000 is considered moderate activity; and $K_i$ of greater than 1000 is considered weak activity.

The $K_i$ (and 95% confidence interval) for compounds of Examples 3, 4, 5, and 8 were 252 (159–396), 680 (470–1000), 166 (83–276), and 83 (55–124), respectively. The compounds of Examples 9–12 also exhibited weak to moderate ability to inhibit limbic D-2 dopamine receptor binding in this procedure.

The compound of Example 5, namely 2,3,4,9-tetrahydro-2-(2-quinolinylethyl)-1H-pyrido[3,4-b]indole, also exhibited significant antipsychotic properties in two other test procedures. In conditioned avoidance response type procedures, the effect of the drug on the subject animals previously trained ability to avoid and/or escape a shock is measured. A compound that blocks the ability of the subject animal to avoid the shock shows potential antipsychotic activity. If the compound blocks the subject animal's ability to escape the shock, then the compound is judged to have a sedative effect.

In this procedure, rats trained previously are placed in plexiglass experimental chambers equipped with a response lever, house light, and sonalert. A steel grid floor is wired for presentation of electric shock. Each trial consists of a fifteen-second warning tone (conditioned stimulus), continuing for an additional fifteen seconds accompanied by electric shock, (unconditioned stimulus). The rat can terminate a trial at any point by depression of the response lever. A response during the initial fifteen-second warning tone ends the trial before shock delivery and is considered an avoidance response, while a response occuring during shock delivery is an escape response. Trials are presented on a variable interval schedule of two minutes. The session consists of sixty trials. Animals are run two to three times weekly with control sessions always preceding a drug run, and with at least one day intervening, compounds are administered i.p. (p.o., s.c.) at appropriate pre-treatment times to a minimum of five to six rats at each dose level over a range of doses.

The following experimental parameters are recorded by computer: (1) the number of intertrial interval responses, (2) the number of avoidance responses, (3) the number of escape responses, and (4) the number of trials in which no response occured. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is assumed to be 100% for avoidance and escape responding and the dose calculated to produce a 50% block in avoidance responding ($AB_{50}$) is obtained from a dose-effect regression line fitted by the method of least squares. Similar calculations are completed to determine the dose at which a 20% inhibition of escape responding ($EB_{20}$) is observed if permitted by the escape response data. If both $AB_{50}$'s and $EB_{20}$'s can be calculated, a dose ratio can be determined according to the following formula:

$$\text{Dose Ratio} = EB_{20}/AB_{50}$$

The compound of Example 5 exhibited antipsychotic properties by blocking the avoidance response in a dose dependant manner at least down to a dose of 15.0 mg/kg i.p. Additionally, the compounds of other examples exhibited antipsychotic properties in this procedure with $AB_{50}$'s as follows: Ex. 4–14.10 i.p.-31.35 o.p.,Ex. 8–30.96 i.p., Ex. 9–22.55 i.p. and Ex. 13–20.87 i.p.

In an alternate conditioned avoidance procedure, in which the animals jump to a shelf to escape, the compounds of Examples 9–12 and 14 demonstrated an ability to block the avoidance response at a dose of 40 mg/kg. i.p.

In the second procedure, the compound's (drug's) abiltiy to antagonize apomorphine-induced stereotyped behavior in mice is measured. In the procedure, 20–25 g male CF-1 mice (Charles River) are tested one week before the experiment for a positive stereotyped response to 10 mg/kg s.c. apomorphine. Test compounds, suspended or solubilized in 0.25% Tween 80 ® in water, are administered at several dose levels to male mice (6/dose level). A control group, run simultaneously with drug groups, receives equal volumes of solvent. Thiry minutes later (i.p. administration) or 60 minutes later (p.o administration), drug-treated and control mice are challenged with 10 mg/kg apomorphine s.c. Five minutes after the injection, the rearing-head-bobbing-licking syndrome induced by apomorphine is recorded as present or absent for each animal. Readings are repeated every 5 minutes during a 30 minute test session. The number of positive or negative 5-minute intervals during which apoomorphine-induced stereotyped behavior is present or absent. $ED_{50}$ values (with 95% confidence intervals) are calculated for inhibition of apomorphine-induced stereotyped behavior, by a simple linear regression analysis with inverse prediction.

The compound of Example 5 exhibited $ED_{50}$'s of 17.99 and 20.37 mg/kg i.p., suggesting a low potential for extrapyramidal side-effect liability. However, this compound did not exhibit activity in this procedure when administered orally to mice at doses up to 127 mg/kg. The compounds of Examples 9–14 were found inactive when tested according to this procedure, thereby similarly suggesting a low potential for extrapyramidol side-effect liability.

The invention includes a method for producing a psychotropic response in a human or animal subject suffering from a condition for which a psychotropic response would be therapeutic, comprising parenterally administering to said subject a psychotropically effective, non-toxic amount of a compound of Example 3, 4, 5 or 8 or a compound of Formula XX or a physiologically acceptable acid addition salt of such compound. The human psychiatric disorders which these compounds may be used to treat are generally classified as psychoses, affective disorders, or anxiety. The compounds of Examples 3, 4, 5, and 8-14 are preferred for producing a psychotropic response. Of these, the compounds of Examples 3, 4, 5 and 8 are particularly preferred and the compound of Example 5 is particularly preferred and the compound of Example 5 is most preferred for producing a psychotropic response. Where used for psychotropic therapy, the dose used will depend upon the form of administration and the compound chosen for the treatment. Furthermore, the dose will vary with the particular host as well as with the age and condition of the host under treatment. Generally, treatment is initiated with small dosages substantially less than the optimum dose of the compound. Thereafter, the dosage is increased by small increments until the optimum effect under the circumstances is reached. In general, the compounds of this aspect of the invention are most desirably administered at a concentration level that will generally afford effective results without causing any harmful or deleterious side-effects. The effective psychotropic amount of the compounds usually ranges from 10-100 micromoles per kilogram of host weight per day.

This invention further includes a method of treating hypertension which comprises administering to a mammal in need thereof an antihypertensively effective amount of a compound of Formula I, or a physiologically acceptable acid addition salt thereof.

The dosage of the compounds of Formula I as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side-effects. The effective antihypertensive amount of the compounds usually ranges from about 0.1 mg to about 300 mg per kilogram body weight per day, although as aforementioned variations will occur. However, a dosage level that is in the range from about 0.5 mg to about 100 mg per kilogram body weight per day is employed most desirably in order to achieve effective results.

When the compounds of Formula I or Formula XX of this invention are used an antihypertensive agents or as antipsychotic agents in mammals, e.g. rats, dogs, mice, and humans, they are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be administered parenterally, preferrably by injection. For parenteral administration they can be used in the form of a sterile solution containing other solutes, for example enough saline or glucose to make the solution isotonic. The following examples further illustrate the manner and best mode of carrying out the invention.

EXAMPLE 1

2,3,4,9-Tetrahydro-2-(4-Pyridinylmethyl)-1H-Pyrido-[3,4-b]Indole, Dihydrochloride Hemihydrate To a stirred suspension of 2,3,4,9-tetrahydro-1H-pyrido[3,4-b]indole(1.3 g, 0.008 mol), freshly baked anhydrous potassium carbonate (3.3 g, 0.024 mol) in 70 mL of dimethyl formamide, was added 1.65 g (0.01 mol) of 4-picolyl chloride, hydrochloride. The reaction mixture was stirred for 1 h. and to this mixture was added 0.39 g (0.0024 mol) of potassium iodide. The reaction mixture was stirred at room temperature overnight, the solvent was removed under vacuum and the solid cake was suspended in 100 mL of water.

The aqueous suspension was extracted with chloroform $(3 \times 100$ mL), the chloroform layer was dried over anhydrous sodium sulfate and was evaporated under reduced pressure. The precipitated solid was separated by filtration, suspended in ethanol and saturated with dry hydrogen chloride. The solvent was concentrated and cooled. The separated solid was filtered and recrystallized from an absolute ethanol-ether (1:1) mixture to afford 0.9 g (36% yield) of the title compound as the hydrochloride salt, mp 175°-178° C.; MS, m/e 263 (M+); NMR (DMSO-$d_6$) $\delta$3(broad, 2H, $CH_2C$), 3.5 (broad, 2H, $CCH_2N$), 3.6 (broad, 1H, exchangeable), 4.5 (s, 2H, $NCH_2$-indole), 4.8 (s, 2H, $NCH_2$ pyridine), 7.1 (m, 2H, indole-H), 7.3 (m, 2H, indole-H), 8.5 (d, 2H, pyridine-H), 9 (D, 2H, pyridine-H), 9.2 (broad, 1H, exchangeable), 10.6 (s, 1H, NH, exchangeable).

Analysis for: $C_{17}H_{17}N_3.2HCl.2HCl.\frac{1}{2}H_2O$:
Calculated: C, 59.13; H, 6.08; N, 12.17
Found: C, 59.16; H, 6.34; N, 11.51

EXAMPLE 2

2,3,4,9-Tetrahydro-2-[2-(4-Pyridinyl)ethyl]-1H-Pyrido[3,4-b]Indole, Dihydrochloride A mixture of 2,3,4,9-tetrahydro-1H-pyrido[3,4-b]indole (1.72 g,0.01 mol),4-vinylpyridine (1.0g, 0.01 mol), and 2 mL of glacial acetic acid were refluxed in 25 mL of methanol for 24 hrs. The solvent was removed in vacuo and the separated solid was suspended in water. The solution was made slightly basic via the addition of solid potassium carbonate and it was extracted with methylene chloride $(4 \times 150$ mL). The methylene chloride layer was dried over anhydrous sodium sulfate and evaporated under reduced pressure to afford 1.2 g (44% yield) of the title compound which was converted to the dihydrochloride salt following the procedure used in Example 1, mp 244°-248° C.; MS, m/e 277 (M+); NMR (DMSO-$d_6$) $\delta$3.1 (broad, 2H, $CH_2$), 3.6 (m,4H,$CCH_2N$ and $NCH_2C$-pyridine), 3.7 (broad, 2H, $CH_2$-pyridine), 3.85 (broad, 1H, exchangeable), 4.6 (broad, 2H, $NCH_2$-indole), 7.1 (t,1H, indole-$\underline{H}$), 7.2 (t, 1H,indole-H), 7.4 (d, 1H, indole-H), 7.5 (d, 1$\overline{H}$, indole-H), 8.1 (d,2H, pyridine-H), 8.9 (d, 2H,pyridine-H), 11.2 (s, NH, exchangeable) and 11.9 (broad, 1H, exchangeable).

Anaylsis for: $C_{18}H_{19}N_3.2HCl$:
Calculated: C, 61.36; H, 5.96; N, 11.93;
Found: C, 60.87; H, 6.11; N, 11.98

EXAMPLE 3

2,3,4,9-Tetrahydro-2-[7-(4-Pyridinyl)heptyl]-1H-Pyrido[3,4-b]Indole, Dihydrochloride Hydrate To a stirred suspension of 2,3,4,9-tetrahydro-1H-pyrido[3,4-b]indole(1.72 g, .01 moles) and freshly baked potassium carbonate (6.6 g, .05 moles) in 60 mL of dimethylformamide was added 5.0 g (.015 moles) of 4-pyridinylheptyl bromide, hydrobromide. The reaction mixture was stirred for 24 hrs, and the solvent was evaporated in vacuo. The residue was extracted in 3×200 mL of methylene chloride, washed with water, dried over anhydrous sodium sulfate and evaporated under reduced pressure. The residue was converted to the dihydrochloride following the procedure used in Example 1 to afford 0.8 g (18.5% yield) of the title compound, mp 101°–106° C.

Analysis for: $C_{23}H_{29}N_3.2HCl.H_2O$:
Calculated: C, 63.01; H, 7.5; N, 9.58; Cl, 16.21;
Found: C, 63.09; H, 6.83; N, 9.53; Cl, 16.10

EXAMPLE 4

2,3,4,9-Tetrahydro-2-[4-(4-Pyridinyl)butyl]-1H-Pyrido[3,4-b]Indole Dihydrochloride The title compound was prepared following the procedure of Example 1 and using 4-pyridinylbutyl bromide hydrobromide instead of 4-picolyl chloride hydrochloride, and was converted to the dihydrochloride, mp 259°–261° C.

Analysis for: $C_{20}H_{23}N_3.2HCl$:
Calculated: C, 63.49; H, 6.61; N, 11.11;
Found: C, 63.16; H, 6.79; N, 10.83

EXAMPLE 5

2,3,4,9-Tetrahydro-2-[2-(2-Quinolinyl)ethyl]-1H-Pyrido[3,4-b]Indole Dihydrochloride A mixture of 2,3,4,9-tetrahydro-1H-pyrido[3,4-b]Indole (1.72 g, 0.01 mol), 2-vinylquinoline (1.5 g, 0.01 mol) and 2 mL of glacial acetic acid were refluxed in 25 mL of ethanol for 24 hrs. The solvent was removed in vacuo and the residue was taken in 4×200 mL of methylene chloride, washed with water and dried over anhydrous sodium sulfate. The methylene chloride was filtered and evaporated under reduced pressure. The separated solid was recrystallized from ethanol to afford 1.6 g (48.9% yield) of the title compound, mp 169°–179° C.; Ms, m/e 327 (M+); NMR (DMSO-D$_6$) δ 3.1 (t, 2H, CH$_2$C), 3.45 (broad, 4H, CCH$_2$N and NCH$_2$ C-quinoline), 4.2 (broad, 2H, CH$_2$-quinoline), 4.3 (broad, 1H, exchangeable), 4.3 (broad 2H, NCH$_2$-indole), 7.1 (t, 1H, indole-H), 7.15 (m, 2H, indole-H), 7.4 (m, 2H, indole-2H), 7.8 (m, 2H, quinoline-H), 8.1 (m, 2H, quinoline-H), 8.8 (m, 2H, quinoline-H), 9.9 (s, 1H, exchangeable) and 11.2 (1H, NH, exchangeable).

Analysis for: $C_{22}H_{21}N_3$:
Calculated: C, 80.73; H, 6.42; N, 12.84;
Found: C, 80.48; H, 6.56; N, 12.87

The dihydrochloride salt was prepared, following the procedure used in Example 1, mp 258°–260° C.

Analysis for: $C_{22}H_{21}N_3.2HCl.\frac{1}{2}H_2O$:
Calculated: C, 64.54; H, 5.86; N, 10.26; Cl, 17.35;
Found: C, 64.81; H, 6.24; N, 10.06; Cl, 17.0

EXAMPLE 6

2,3,4,9-Tetrahydro-2-[4-(4-Quinolinyl)butyl]-1H-Pyrido[3,4-b]Indole, Dihydrochloride The title compound was prepared following the procedure of Example 1 and using 4-quinolinylbutyl bromide hydrobromide instead of 4-picolyl chloride hydrochloride and was converted to the dihydrochloride salt, mp 180°–182° C.

Analysis for: $C_{24}H_{25}N_3.2HCl.H_2O$:
Calculated: C, 64.57; H, 6.50; N, 9.41;
Found: C, 64.78; H, 6.30; N, 9.33

EXAMPLE 7

2,3,4,9-Tetrahydro-2-[2-(2Pyrazinyl)ethyl]-1H-Pyrido[3,4-b]Indole, Dihydrochloride The title compound was prepared following the procedure for Example 2 and using 2-vinylpyrazine instead of 4-vinylpyridine and was converted to the dihydrochloride, mp 266°–269° C.

Analysis for: $C_{17}H_{18}N_4.2HCl$:
Calculated: C, 58.11; H, 5.69; N, 15.95;
Found: C, 58.67; H, 5.82; N, 15.79

EXAMPLE 8

2,3,4,9-Tetrahydro-2-[4-(2-Quinolinyl)butyl]1H-Pyrido[3,4-b]Indole, Dihydrochloride The title compound was prepared following the procedure of Example 1 and using 2-quinolinylbutylbromide hydrobromide instead of 4-pilolyl chloride hydrochloride and was converted to the dihydrochloride salt, m.p. 210°–215° C.

Analysis for: $C_{24}H_{25}N_3.2HCl.\frac{1}{2}H_2O$:
Calculated: C, 63.29; H, 6.59; N, 9.20; Cl, 15.60;
Found: C, 63.12; H, 6.29; N, 9.05; Cl, 15.57

EXAMPLE 9

2,3,4,9-Tetrahydro-2-[2-(2-Pyridinyl)ethyl]-1H-pyrido[3,4-b]-indole, Dihydrochloride.

A mixture of 2,3,4,9-tetrahydro-1H-pyrido[3,4-b]indole (1.72 g, 0.01 mol), 2-vinylpyridine (1.0 g,. 01 ml,) and 2 mL of glacial acetic acid were refluxed in 25 mL of methanol for 24 hrs. The solvent was removed in vacuo and the separated solid was suspended in water. The solution was made slightly basic via the addition of solid potassium carbonate and it was extracted with methylene chloride (4×150 mL). The methylene chloride layer was dried over anhydrous sodium sulfate and evaporated under reduced pressure to afford 1.2 g (44% yield) of the title compound which was converted to the dihydrochloride salt m.p. 212°–215° C.

Analysis for: $C_{18}H_{19}N_3.2HCl.\frac{1}{2}H_2O$:
Calculated: C, 60.16; H, 6.12; N, 11.69;
Found: C, 60.72; H, 6.02; N, 11.48

EXAMPLE 10

6-Fluoro-2,3,4,9-Tetrahydro-2-[2-(4-Pyridinyl)ethyl]1H-pyrido[3,4-b]indole, dihydrochloride, hemihydrate The title compound was prepared following procedure of Example 9, using 4-vinylpyride (3.0 g, 0.0157 mol) instead of 2-vinylpyridine and 6-fluoro-2,3,4,9-tetrahydro-1H-pyrido[3,4-b]indole. The free base was recovered first and was then converted to the dihydrochloride salt (3.8 g, 82.6% yield) m.p. 173° 176° C.

Analysis for: $C_{18}H_{18}FN_3.2HCL.\frac{1}{2}H_2O$:

Calculated: C, 57.20; H, 5.61; N, 11.13; Cl, 18.79;
Found: C, 56.44; H, 5.72; N, 11.02; Cl, 18.88

EXAMPLE 11

6-Fluro-2,3,4,9-Tetrahydro-2-[2-(2-Pyridinyl)ethyl]1H-pyrido[3,4-b]indole, dihydrochloride The title compound was prepared following procedure of Example 9, using 6-fluoro-2,3,4,9-tetrahydro-1H-pyrido[3,4-b]indole (3.0 g, 0.0157 mol) instead of 2,3,4,9-tetrahydro-1H-pyrido[3,4-b]indole and 2-vinylpyridine (3 ml., 0.028 mol). The free base was recovered first and was then converted to the dihydrochloride salt (3.4 g, 73.9% yield), m.p. 234°–236° C.

Analysis for: $C_{18}H_{18}FN_3.2HCL$:
Calculated: C, 58.68; H, 5.47; N, 11.41, Cl, 19.25;
Found: C, 58.17; H, 5.46; N, 11.30; Cl, 19.02

EXAMPLE 12

6-Fluoro-2,3,4,9-Tetrahydro-2-[2-(2-Quinolinyl)ethyl]1H-pyrido[3,4-b]indole, dihydrochloride hemohydrate The title compound was prepared following procedure of Example 9, using 2-vinylquinoline (4.0 g, 0.025 mol) instead of 2-vinylpyridine and 6-fluoro-2,3,4,9-tetrahydro-1H-pyrido[3,4-b]indole (3.3. g, 0.017 mol). The free base was recovered first and then converted to the dihydrochloride salt (3.4 g, 58.6% yield), m.p. 266°–269° C.

Analysis for: $C_{22}H_{20}FN_3.2HCl.\frac{1}{2}H_2O$:
Calculated: C, 61.83; H, 5.43; N, 9.85; Cl, 16.59;
Found: C, 61.92; H, 5.61; N, 9.57; Cl, 16.21

EXAMPLE 13

2,3,4,9-Tetrahydro-2-[3-(3-Pyridinyl)propyl]1H-pyrido[3,4-b]indole, dihydrochloride To a stirred suspension of 2,3,4,9-tetrahydro-1H-pyrido[3,4-b]indole (1.3 g, 0.008 mol) freshly baked anhydrous sodium carbonate (1.7 g, 0.016 mol) and catalytic amount of cesium carbonate in 70 mL of dimethylformamide, was added 2.10 g (0.016 mol) of 3-pyridinylpropylbromide, hydrobromide.

The reaction was stirred overnight at room temperature, then the solvent was removed under vacuum and the solid cake was suspended in 100 mL of water and extracted with methylene chloride (3×100 mL).

The methylene chloride extracts were combined, dried over anhydrous sodium sulfate and evaporated under reduced pressure. The title compound was separated by HPLC using ethyl acetate as the eluent to afford 2.1 g (92% yield) of the title compound which was converted to the dihydorchloride salt; mp. 257°–260° C.

Analysis for: $C_{19}H_{21}N_3.2HCl$:
Calculated: C, 62.63; H, 6.32; N, 11.54;
Found: C, 62,17; H, 6.28; N, 11.49.

EXAMPLE 14

2,3,4,9-Tetrahydro-2-[3-(4-Pyridinyl)propyl]1H-pyrido[3,4-b]indole, dihydrochloride The title compound was prepared following the procedure of Example 13, using 4-pyridinylpropyl bromide, hydrobromide (5.0 g, 0.025 mol) instead of 3-pyridinyl-propylbromide, hydrobromide to react with 2,3,4,9-tetrahydro-1H-pyrido[3,4-b]indole (3.0 g, 0.017 mol). The free base was recovered first and was then converted to the hydrochloride salt (2.0 g, 40.8% yield), m.p. 271°–273° C.

Analysis for: $C_{19}H_{21}N_3.2HCL.\frac{1}{2}H_2O$;
Calculated: C, 61.12; H, 6.40; N, 11.26;
Found: C, 61.11; H, 6.54, N, 11.73

What is claimed is:

1. A compound of the formula:

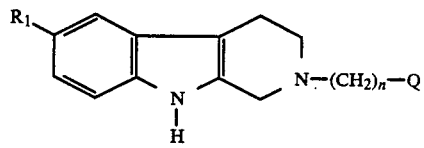

wherein Q represents

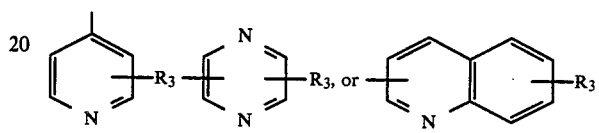

in which $R_3$ is hydrogen, $C_{1-4}$ alkyl, $C_{1-4}$ alkoxy, or —$COO(C_{1-2})$ alkyl, and n is an integer from 1 to 7; and $R_1$ is a hydrogen, halogen, hydroxy, or $C_{1-3}$ alkyl, or physiologically acceptable acid addition salts thereof, providing however, that when n is 1, Q may not be quinolinyl.

2. A compound of claim 1 in which n is 2, 4 or 7.

3. A compound of claim 1 in which $R_1$ is hydrogen or fluorine.

4. A compound of claim 1 in which $R_3$ is hydrogen.

5. A compound of claim 1 in which Q is pyrazinyl.

6. A compound of claim 1 in which Q is 2- or 4-quinolinyl.

7. A compound of claim 1 selected from a group consisting of 2,3,4,9-tetrahydro-2-[7-(4-pyridinyl)heptyl]-1H-pyrido[3,4-b]indole, 2,3,4,9-tetrahydro-2-[4-(4-pyridinyl)butyl]-1H-pyrido[3,4-b]indole, and 2,3,4,9-tetrahydro-2-[2-(2-quinolinyl)ethyl]-1H-pyrido[3,4-b]indole or physiologically acceptable acid addition salts thereof.

8. A compound of claim 1 selected from a group consisting of 2,3,4,9-tetrahydro-2-[2-(4-pyridinyl)ethyl]-1H-pyrido[3,4-b]indole, 2,3,4,9-tetrahydro-2-[4-(4-pyridnyl)butyl]-1H-pyrido[3,4-b]indole, 2,3,4,9-tetrahydro-2-[2-(2-quinolinyl)ethyl]-1H-pyrido[3,4-b]indole, 2,3,4,9-tetrahydro-2-[4-(4-quinolinyl)butyl]-1H-pyrido[3,4-b]indole, 2,3,4,9-tetrahydro-2-[2-(2-pyrazinyl)ethyl]-1H-pyrido[3,4-b]indole, 6-fluoro-2,3,4,9-tetrahydro-2-[2-(4-pyridinyl)ethyl]-1H-pyrido[3,4-b]indole, 6-fluoro-2,3,4,9-tetrahydro-2-[2-(2-quinolinyl)ethyl]-1H-pyrido[3,4-b]indole, and 2,3,4,9-tetrahydro-2-[3-(4-pyridinyl)propyl]-1H-pyrido[3,4-b]indole, or physiologically acceptable acid addition salts thereof.

9. A method of treating hypertension comprising administering to a mammal in need thereof an antihypertensively effective amount of a compound of claim 1.

10. A method for producing a psychotropic response in a human or animal subject suffering from a condition for which a psychotropic response would be therapeutic, comprising administering to said subject a psychotropically effective, non-toxic amount of a compound selected from a group consisting of:
- 2,3,4,9-tetrahydro-2-[7-(4-pyridinyl)heptyl]-1H-pyrido[3,4-b]indole,
- 2,3,4,9-tetrahydro-2-[4-(4-pyridinyl)butyl]-1H-pyrido[3,4-b]indole,
- 2,3,4,9-tetrahydro-2-[2-(2-quinolinyl)ethyl]-1H-pyrido[3,4-b]indole,
- 2,3,4,9-tetrahydro-2-[4-(2-quinolinylbutyl]-1H-pyrido[3,4-b]indole,
- 6-fluoro-2,3,4,9-tetrahydro-2-[2-(4-pyridinyl)ethyl]-1H-pyrido[3,4-b]indole,
- 6-fluoro-2,3,4,9-tetrahydro-2-[2-(2-quinolinyl)ethyl]-1H-pyrido[3,4-b]indole,
- 2,3,4,9-tetrahydro-2-[3-(4-pyridinyl)propyl]-1H-pyrido[3,4-b]indole, or physiologically acceptable acid addition salts thereof.

11. A method according to claim 10 in which the compound administered is 2,3,4,9-tetrahydro-2-[2-(2-quinolinyl)ethyl]-1H-pyrido[3,4-b]indole or a physiologically acceptable acid addition salt thereof.

12. A compound of the formula

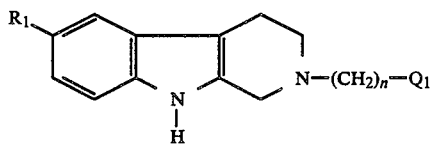

XX wherein
n is an integer from 1 to 7;
$R_1$ is hydrogen, halogen, hydroxy, or $C_{1-3}$ alkyl; and
$Q_1$ is 2- or 3-pyridinyl, or physiologically acceptable acid addition salts thereof.

13. A compound according to claim 12 in which $R_1$ is hydrogen or halogen.

14. A compound according to claim 12 in which $R_1$ is fluorine.

15. A compound according to claim 12 in which n is 2, 3 or 4.

16. A compound according to claim 12 selected from a group consisting of
- 2,3,4,9-tetrahydro-2-[2-(2-pyridinyl)ethyl]-1H-pyrido[3,4-b]indole,
- 6-fluoro-2,3,4,9-tetrahydro-2-[2-(2-pyridinyl)ethyl]-1H-pyrido[3,4-b]indole, and
- 2,3,4,9-tetrahydro-2-[3-(3-pyridinyl)propyl]-1H-pyrido[3,4-b]indole, or physiologically acceptable acid addition salts thereof.

17. A method of producing a psychotropic response in a human or animal subject suffering from a condition for which a psychotropic response would be therapeutic, coprising parentally adminsistering the said subject a psychotropically effective, non-toxic amount of a compound of the formula

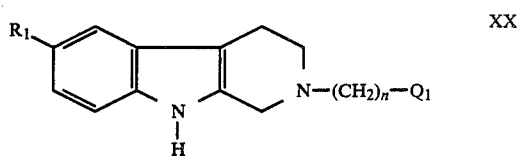

XX wherein
n is an interger from 1 to 7;
$R_1$ is hydrogen, halogen, hydroxy, or $C_{1-3}$ alkyl; and
$Q_1$ is 2- or 3-pyridinyl,
or physiologically acceptable acid addition salts thereof.

18. A method according to claim 17 in which $R_1$ is hydrogen or halogen.

19. A method according to claim 17 in which $R_1$ is fluorine.

20. A method according to claim 17 in which n is 2, 3 or 4.

21. A method according to claim 17 in which the compound is selected from a group consisting of:
- 2,3,4,9-tetrahydro-2-[2-(2-pyridinyl)-ethyl]-1H-pyrido[3,4-b]indole,
- 6-fluoro-2,3,4,9-tetrahydro-2-[2-(2-pyridinyl)ethyl]-1H-pyrido[3,4-b]indole, and
- 2,3,4,9-tetrahydro-2-[3-(3-pyridinyl)-propyl]-1H-pyrido[3,4-b]indole, or physiologically acceptable acid addition salts thereof.

* * * * *